(12) United States Patent
Schaff et al.

(10) Patent No.: US 6,219,440 B1
(45) Date of Patent: Apr. 17, 2001

(54) METHOD AND APPARATUS FOR MODELING CELLULAR STRUCTURE AND FUNCTION

(75) Inventors: James C. Schaff, Cheshire; John Carson; Leslie Loew, both of West Hartford, all of CT (US)

(73) Assignee: The University of Connecticut, Storrs, CT (US)

( * ) Notice: Subject to any disclaimer, the term of this patent is extended or adjusted under 35 U.S.C. 154(b) by 0 days.

(21) Appl. No.: 09/008,649

(22) Filed: Jan. 16, 1998

Related U.S. Application Data

(60) Provisional application No. 60/036,185, filed on Jan. 17, 1997.

(51) Int. Cl.[7] ............................................. G06K 9/00
(52) U.S. Cl. ...................................... 382/128; 703/11
(58) Field of Search ............................... 382/128, 133, 382/135, 130, 131, 154; 364/578; 395/500; 600/410, 416; 128/710; 703/11, 2

(56) References Cited

U.S. PATENT DOCUMENTS

| | | |
|---|---|---|
| 4,841,479 | 6/1989 | Tsuji et al. . |
| 4,945,478 * | 7/1990 | Merickel et al. .................... 382/131 |
| 5,025,388 | 6/1991 | Cramer, III et al. . |
| 5,029,119 | 7/1991 | Konno . |
| 5,273,038 * | 12/1993 | Beavin ................................. 600/416 |
| 5,307,287 | 4/1994 | Cramer, III et al. . |
| 5,424,963 | 6/1995 | Turner et al. . |
| 5,446,652 | 8/1995 | Peterson et al. . |
| 5,446,860 | 8/1995 | Dresser et al. . |
| 5,446,870 | 8/1995 | Hinsberg, III et al. . |
| 5,826,065 | 10/1998 | Hinsberg, III et al. . |
| 5,914,891 * | 6/1999 | McAdams et al. .................... 703/11 |
| 5,947,899 * | 9/1999 | Winslow et al. .................... 600/410 |

* cited by examiner

*Primary Examiner*—Joseph Mancuso
*Assistant Examiner*—Vikkram Bali
(74) *Attorney, Agent, or Firm*—Cantor Colburn LLP

(57) ABSTRACT

A method of simulating a biological material.

22 Claims, 9 Drawing Sheets

Experimental Images

Mouse Neuroblastoma loaded with Indo 1

Applied Bradykinin at t=0 t = 6 seconds t = 7 seconds t = 8 seconds t = 9 seconds t = 10 seconds (Images Courtesy of Charles Fink)

METHOD AND APPARATUS FOR MODELING CELLULAR STRUCTURE AND FUNCTION

CROSS REFERENCE TO RELATED APPLICATIONS

This application claims priority of U.S. Provisional patent application Ser. No. 60/036,185 filed Jan. 17, 1997.

BACKGROUND OF THE INVENTION

1. Field of the Invention

The invention relates in general to cell simulation and in particular to a method and apparatus for modeling cellular structure and function which produces simulation data that is easily comparable to experimental data.

2. Prior Art

Tools such as fluorescent probes and confocal microscopy have enabled the resolution of three dimensional intracellular spatial distribution of different molecular species as well as sub-cellular structures. Research in cellular physiology requires the formation of theoretical hypotheses regarding the experimentally observed phenomena. These hypotheses are often formalized into mathematical models, and then tested by incorporating these models into simulations.

The deficiencies in existing technology originates from the current limitations of the cellular representation. Cells are represented as ideal and simple geometric shapes consisting of spatially homogeneous behavior (physiology) and structure (anatomy). This prevents the researcher from expressing an observed physiological phenomena in a simulation that maps easily to an actual experiment of an intact cell. Thus the validation of the model, and hence the hypothesis, is made very difficult.

Most current efforts in the modeling and simulation of cellular physiology are directed toward either very specific models of individual mechanisms or abstract representations of more complex phenomena. The specific models include models of individual molecular interactions such as ion channels gathered from biochemistry and electrophysiology research. The abstract models apply simplifications of the underlying mechanisms that are usually only appropriate to explain a small class of physiological problems.

Some typical abstractions include simplified simulation geometry, such as cable theory applied to nerve action potentials (where elementary features are uniform cross sections of nerve processes), or spatially homogenous grids with cell boundaries defined by geometric primitives (planes, spheres, cylinders). Additional abstractions include representing complex physiology in terms of a small number of variables with terms that try to approximate the overall effect of the underlying physiology (simple models of cellular signaling such as calcium dynamics).

Efforts to address the complexity of physiology also tend to concentrate on intercellular phenomena. The cellular automata approach looks at intercellular interactions where the fundamental computational unit represents an entire cell. There has also been numerous simulations in neurophysiology involving models based on cable theory. These models decompose a single neuronal cell into computational elements representing entire cross sections of axons and dendrites. While these models reproduce the external behavior of action potentials in neurons with good fidelity, the inherent geometric simplicity of the formulation restrict their application to the class of problems where the cell interior can be considered a completely homogenous conductive media.

Interest has been shown in the collection of current physiological knowledge in a computer usable form. An example of this is SENEX, a computer based representation of cellular signal transduction processes in the central nervous system. This is an object oriented classification structure of biologic entities and significant relationships among them. However, their representation of biological entities and relationships are not in the form of actual mathematical models, and thus can not be used directly for simulations.

Present technology lacks good spatial correlation from simulation to empirical data. Typical simulations utilize an idealized geometry such as a cylinder, sphere, or plane rather than representing the geometry of an actual cell. The simulations are also spatially homogeneous, thus every part of the simulation has the same basic behavior, in contrast with actual cells. Thus, comparison of simulation with experiment is difficult or impossible.

SUMMARY OF THE INVENTION

The above-discussed and other drawbacks and deficiencies of the prior art are overcome or alleviated by the method and apparatus for modeling cellular structure and function of the present invention. The present invention incorporates a theoretical hypotheses of cellular physiology into a simulation framework that allows direct comparison of simulation results with experimental data. The description of the biological model is kept independent of the solution by the use of an integrated anatomical and physiological modeling language. This framework allows complex heterogeneous intracellular chemical simulations to be built with little or no knowledge of the underlying numerical methods. Because the simulation results are easily compared to the experimental results, the user can more easily confirm the hypothesis.

The above-discussed and other features and advantages of the present invention will be appreciated and understood by those skilled in the art from the following detailed description and drawings.

BRIEF DESCRIPTION OF THE DRAWINGS

Referring now to the drawings wherein like elements are numbered alike in the several FIGURES.

DETAILED DESCRIPTION OF THE INVENTION

Figure 1:
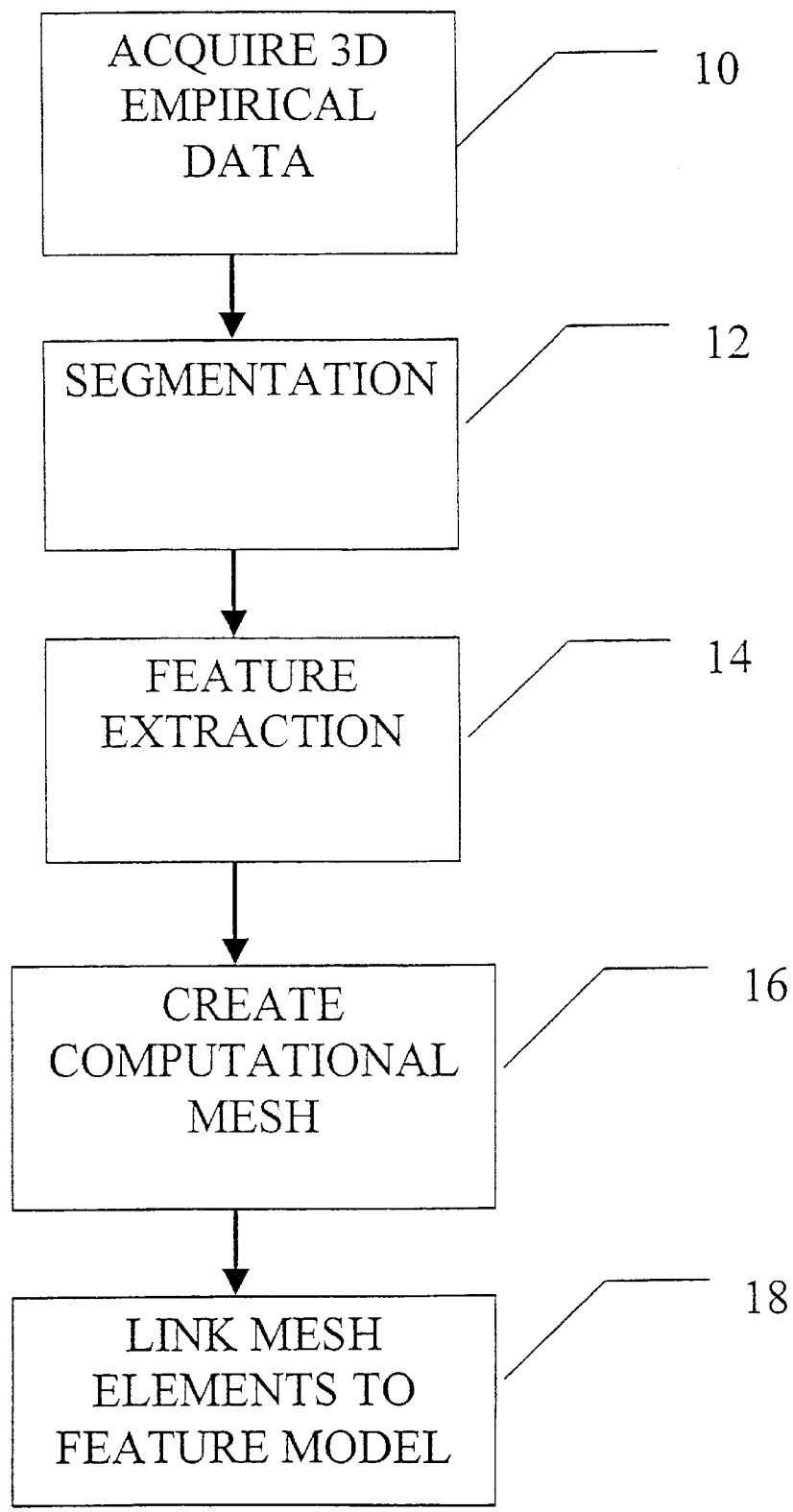
FIG. 1 is a flowchart of the method for creating the simulation volume.
Figure 2:
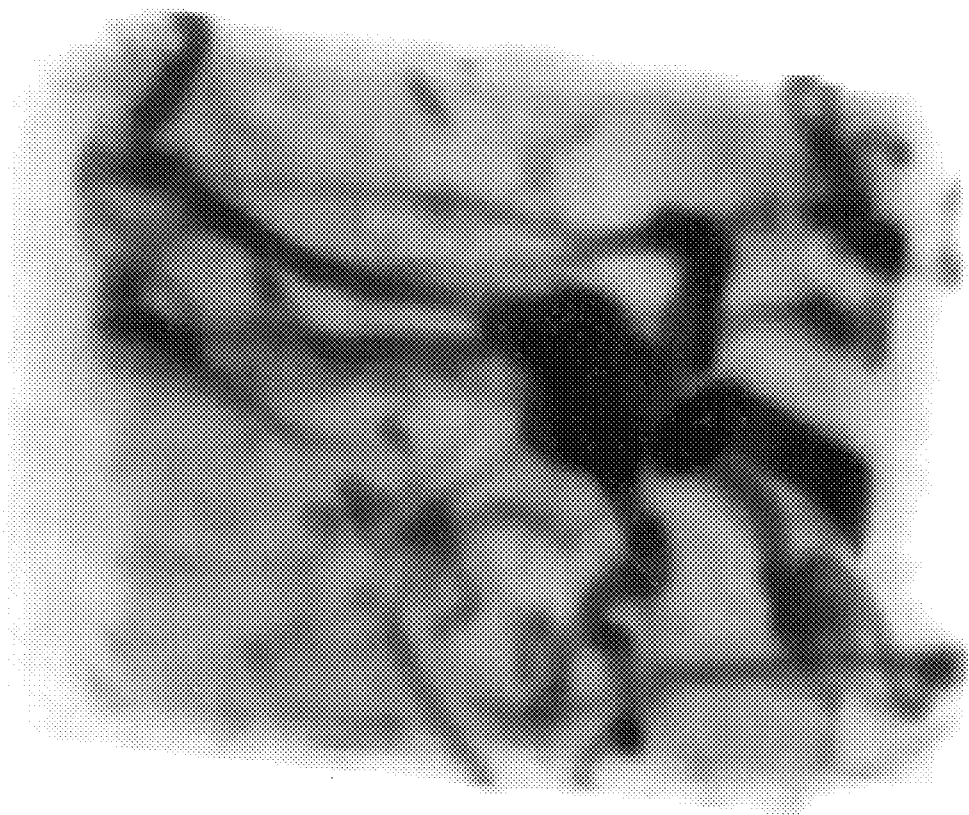
FIG. 2 is an illustration of a three dimensional image from a confocal microscope.
Figure 3:
FIG. 3 is an illustration of the image of FIG. 2 segmented.
Figure 4:
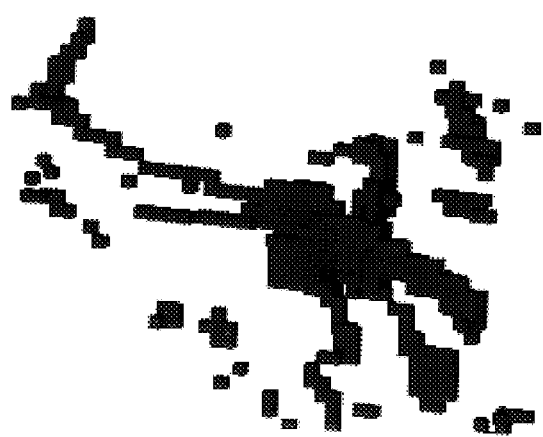
FIG. 4 is an illustration of a three dimensional volume of simulation elements derived from the segmented image in FIG. 3.
Figure 5:
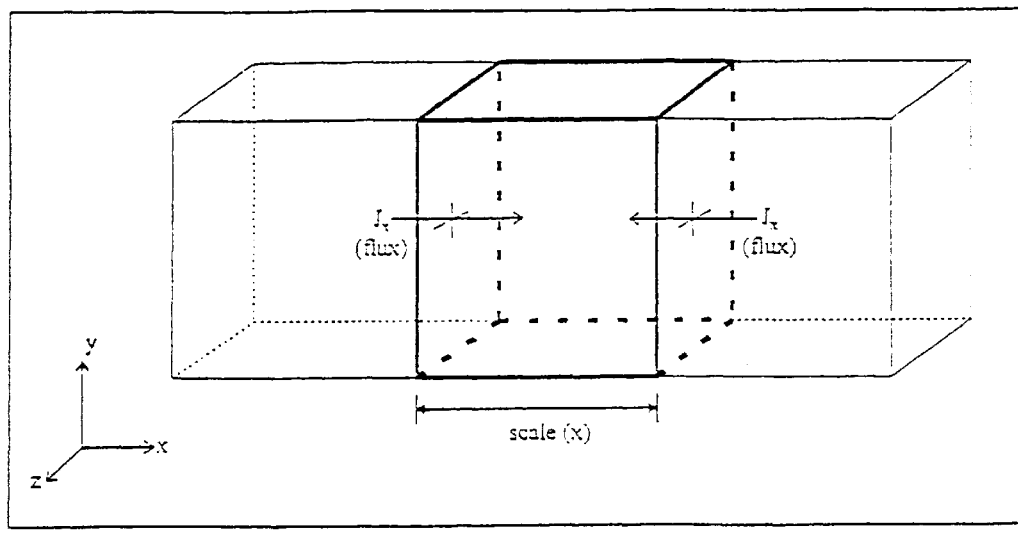
FIG. 5 is an illustration of three simulation elements using an orthogonal finite volume approach.

The invention is directed to simulation of cellular physiological and anatomical parameters. The invention first creates a simulation domain based on an actual image of the cell. A simulation volume is created and then simulation is performed by modeling the behavior, physiological and/or anatomical, of each simulation element making up the simulation volume. FIG. 1 is a flowchart of the routine performed to create the simulation volume. At step 10, three dimensional empirical data of the cell is acquired using known techniques (e.g. confocal microscopy). FIG. 2 is an exemplary three dimensional image from a confocal microscope. It is understood that the source of the empirical data may be other than a confocal microscope. The cell is isolated through a three dimensional segmentation step 12 and the cellular physiology is determined at feature extraction step 14. FIG. 3 is a three dimensional image showing the result of the segmentation operation which includes thresholding the image to isolate the cell. At step 16, the three dimensional empirical data is used to generate a simulation volume made up of a plurality of simulation elements or other computational meshes. FIG. 4 is a diagram of the three dimensional simulation volume created from the segmented image of FIG. 3 which corresponds to features acquired from the original image. Three simulation elements are shown in FIG. 5. The simulation volume is created by sampling the three dimensional empirical data to form a plurality of simulation elements. Each simulation element represents only the physiology of a single class of cellular features determined in the feature extraction step 14. Lastly, at step 18 each simulation element is then linked to a stored model corresponding to the physiology of the simulation element. The models used are described in more detail below. In this way, the simulation volume is made up of a plurality of simulation elements, each being associated with a model describing its behavior.

An important aspect of the present invention is the utilization of three dimensional empirical data and images to directly build the simulation model. The anatomical features of the cell are identified and extracted as geometric descriptions. These geometric descriptions are sampled to create a simulation volume. This simulation volume represents a spatially heterogeneous collection of three dimensional simulation elements as shown in FIGS. 4 and 5, where each simulation element corresponds to each identified anatomical feature in position and function. Comparison of simulation results and observed behavior is facilitated because the microscopy data and the simulation model are mapped onto the same geometry. Geometric models, simulation elements, and original 3D images can all be rendered into the same 3D scene. They are all mapped to the same coordinate system for ease of viewing and comparison. In addition, both the simulation elements and the empirical data can be formatted as series of images that can be viewed easily. Simulation results can be directly correlated with experimental time series volume datasets. Thus, the model can be modified until the experimental results are duplicated. The same physiological models can be verified in multiple experiments (different geometry and different stimuli). The present invention provides a framework for encapsulating knowledge about the interaction of intracellular components.

In accordance with another important aspect of the invention, by generating a simulation volume in which each element corresponds to a single class of physiological features, simulation of the entire cell is simplified. Current simulation efforts establish a model as a single set of ordinary and partial differential equations that represents all cellular physiology of interest. This requires more complex mathematical descriptions and the resulting interactions between simulation elements are not as easily separable in terms of their physiological origins. The present invention establishes the simulation as a spatially heterogeneous collection of simulation elements as shown in FIG. 5, where each element represents only the physiology of a single class of cellular features. This allows complex behavior to be simulated using a collection of simple models. Each simple model maps directly to a biological feature and encapsulates only the physiology associated with that feature. The model describes how it varies the concentration of each molecular species within the bounds of an element and how it interacts with its immediate environment. Thus, an assembly of different elements can interact with complex behavior even though their individual behavior may be simple. This organization more closely approximates the actual dynamics within the cell and allows the modeling of each feature to be independent, and therefore simpler.

Yet another important aspect of the invention is the use of abstract physiological models in developing classes of biological entities. An example is a feature model which encapsulates the physiological behavior corresponding to a single area or compartment (endoplasmic reticulum, nucleus, cytosol, extracellular, etc.) within a particular cell type. The process of creating a library of accepted feature models can be a powerful tool for encapsulating knowledge of general physiological function.

Each feature consists of a collection of reaction models and molecular species models and the behavior of the resulting feature model is the result of these coupled reactions. These reactive models are categorized as volume reactions (i.e. reactions within an element) and membrane reactions (e.g. pumps and channels including binding and trans-membrane fluxes). As an example, an IP3 receptor (membrane reaction model) may be specified as part of an endoplasmic reticulum feature.

The modeling framework defines a variety of components including the reaction models to be used, initial conditions and other parameters described herein. The user defines the modeling framework using either a cellular simulation description language or a graphical user interface.

In an exemplary embodiment of the invention, a cellular simulation description language has been implemented where the geometry is based on a subset of Silicon Graphic's Inventor® 3D Scene Description Language, extended to deal with constructive solid geometry and volume datasets. This language was then further extended to introduce biological descriptions and a simulation definition. A graphical abstraction of these files has been generated to allow more natural interaction with the models and simulation results. This interactive graphical user interface provides some model analysis tool as well as simulation control.

Yet another important aspect of the invention is the use of a model geometry that corresponds exactly with the geometry of the empirical volumetric data. The spatial organization of cellular structure is represented by a collection of feature models that correspond to identified cellular features. These cellular features can be identified by three dimensional segmentation and feature extraction from confocal microscopy data. The feature extraction is simplified if cellular structures are labeled using fluorescent probes that are specific to that structure.

For cellular structure that is either too small (e.g. mitochondria) or too convoluted (e.g. endoplasmic reticulum) to be extracted easily from actual data, feature geometry may be approximated by synthetic geometry. This synthetic geometry can consist of any combination of geometric primitives (e.g. sphere, cylinder), mathematically defined solid models (e.g. fractal solids), or arbitrary polygonal surfaces (e.g. CAD models). Alternatively, features that are too small for appropriate representation may be assumed to be evenly distributed within the cell compartment (e.g. ER may be continuously distributed within cytosol) while maintaining separate models for the compartment feature and the evenly distributed feature. Once features are extracted, they are classified by their underlying physiology, and are linked to the appropriate feature models for use in simulation.

The invention may simulate chemical dynamics, mechanical dynamics or a combination of chemical and mechanical dynamics. The model of species interaction for simulating chemical dynamics includes diffusion in the presence of an electric field, chemical reactions, and membrane transactions due to pumps and channels. Prior to describing the chemical dynamics model in detail, concepts underlying the diffusion in the presence of an electric field will be described.

The model consists of a set of continuous equations relating the state variables of the system and the input (stimuli). The set of state variables consists of the concentrations of each molecular species $C_i$ and the electric potential V defined over a subset of three dimensional space for time greater than zero. State variables are defined such that knowledge of their values at time t=T is sufficient to determine the behavior of the whole model at any time t>T for any known stimulus. In general, the model itself can be a function of position (heterogeneous) and also of the state variables (nonlinear).

The model uses electrodiffusion/reaction equations to determine molecular flux. According to the Nernst-Plank Equation, the molecular flux $\vec{J}_i$ due to diffusion and electric forces is as described in equation (1). Note that the subscript i denotes values pertaining to the $i^{th}$ molecular species.

$$\vec{J}_i = -D_i \nabla C_i - z_i \mu_i C_i \nabla V, \quad \text{where } \mu_i = \frac{D_i F}{RT} \quad 1)$$

Where $C_i$ is the concentration, $D_i$ is the diffusion constant, $z_i$ is the ionic valence, $m_i$ is the mobility, V is the electric potential, F is Faraday's constant, R is the gas constant, and T is the absolute temperature. The first term of (1) describes the diffusion flux, the second term of (1) describes the flux due to the electric field.

The time rate of change of species concentration defined over an infinitesimally small volume is the sum of the net flux into the volume and the net reaction rate $$\frac{\partial C_i}{\partial t} = -\nabla \cdot (\vec{J}_i) + S_i(C_1, C_2, \ldots C_N) \quad 2)$$

where $S_i$ defines the net chemical reaction rate for species $C_i$.

The model also uses electrical potential equations to define electric flux density. The electric potential can be defined everywhere according to the laws of electrostatics. Gauss's law (3) states that the net charge Q within a closed surface is equal to the net electric flux density $\vec{D}$ leaving that surface.

$$Q = \oint_S \vec{D} \cdot d\vec{S} \quad 3)$$

and $\vec{D}$ is related to the permittivity (or dielectric constant) e, the electric field $\vec{E}$ and electric potential V according to $$\vec{D} = \epsilon \vec{E} = -\epsilon \nabla V \quad 4)$$

The total charge within a volume can be defined as the concentration of molecular species $C_i$, the ionic valence $z_i$, and Faraday's constant F integrated over that volume.

$$Q = \oint_V \left[ \sum_i z_i F C_i \right] dv \quad 5)$$

Combining (3), (4) and (5) gives a form of Gauss's Law (6) that can be evaluated for an incremental volume and relates electric potential to ionic concentrations.

$$\oint_V \left[ \sum_i z_i F C_i \right] dv = \oint_S (-\epsilon \nabla V) \cdot d\vec{S} \quad 6)$$

The electric potential can also be defined as a function of electric currents through a conductive media and across capacitive boundaries. Conservation of charge states that in a conductor, the net current density $\vec{J}$ leaving any closed surface $d\vec{S}$ is equal to 0. This formulation assumes that the interior of all connected regions within a cell simulation (cytosol, ER lumen, extracellular milieu, etc.) can be modeled as conductors. This implies that the relaxation time of a free charge placed in the interior (lumen) to the surface (membrane) is much faster than the cellular dynamics of interest.

$$-\frac{dQ}{dt} = \oint_S \vec{J} \cdot d\vec{S} = 0 \quad 7)$$

$\vec{J}$ is related to the conductance 1, and the electric potential V according to Ohm's Law (8)

$$\vec{J} = -\lambda \nabla V \quad \text{where } \lambda = \sum_i z_i \mu_i C_i \quad 8)$$

for the interior of a conductor (Cell or organelle body), and for the current density normal to a membrane $J_n$ is related to the membrane specific capacitance Cm, and the net charge flux density passing through the membrane Jm (via pumps, channels, etc.) according to $$J_n = -C_m \frac{\partial (V - V_{opposite})}{\partial t} + J_m \quad 9)$$

substituting (8) and (9) into (7) gives a form of conservation of current that can be applied to both membranes and interior spaces with less geometric constraints than standard cable theory.

The specific chemical dynamics simulation will now be described. The specification of the chemical dynamics simulation is very flexible. The simulation description specifies the molecular species to be simulated, parameters to be logged, the number of elements in each dimension, the size of the elements, and the simulation time step. A chemical dynamics simulation is created by sampling all or part of the model geometry into a three dimensional mesh of simulation elements. FIG. 5 shows three elements of a uniform orthogonal mesh. The chemical dynamics are modeled at the concentration level where dynamics is described as fluxes of molecular species across boundaries separating adjacent elements and chemical reactions within the same element as shown FIG. 6. These fluxes can be functions of diffusion, ion drift, membrane potential, membrane transport (including pumps and channels) or any other relationship involving the spatial distribution of molecular species. Membranes may be represented by element boundaries separating dissimilar elements. The state variables consist of the concentration distribution of every molecular species as well as membrane potential.

The chemical dynamics are described as reactions with elements and fluxes of molecular species across boundaries separating adjacent elements. These fluxes can be functions of diffusion, ion drift, membrane potential, chemical reaction, or any other relationship involving the spatial distribution of molecular species. Membranes are represented by element boundaries separating dissimilar elements. The collection of all concentrations of each molecular species within each simulation element and the electric potential in each simulation element constitutes the state variables of the system.

The number of species defined in a simulation will affect the complexity of the model used for the simulation. Each additional species introduces complexity in two ways.

(1) One or more chemical reactions in the model may become active in the simulation if the additional species complete the minimum set of reagents/products.

(2) Active reaction models may assume a more complicated form that incorporates the effects of the additional species.

Both local and membrane reactions are constructed of a hierarchical assembly of models (rate equations) of differing complexity. The model selected for a given reaction is the simplest form that incorporates all of the relevant reagents currently defined by a simulation.

The numerical solution to all of the model equations is achieved by a conventional finite volume method. This method is based on the sub-domain formulation of the method of weighted residuals, although the resulting discrete equations resemble those of the finite- difference method. The finite volume method allows for very good control of boundary conditions and profile assumptions while preserving the conservative nature of many of the equations of interest. Examples of models exhibiting conservative behavior is Fick's Law and Gauss's Law, which mandates conservation of mass flux and electric flux density respectively.

The fundamental step in the numerical solution of a set of equations involves integrating them in time and over space over a single volume element using appropriate interpolation profiles and boundary conditions. The solution of each integration relates a small neighborhood of sample values over space and time. As shown in FIG. 5, boundary conditions for individual elements in the chemical simulation framework guarantee mass conservation. The flux is calculated by the Nernst-Plank equation when the neighboring elements are of similar type. The flux is based on membrane reactions (channels, pumps . . . ) when the neighboring elements are different.

The resulting equations are solved by an implicit method using an iterative solution by the line by line method. This is an implicit method that guarantees stability when the models used in the simulation obeys some simple and physically appropriate constraints. The ability of each iteration to converge to the solution of the non-linear equations is made possible by adaptive underrelaxation scheme. The simulation geometry is assumed to be uniformly sampled orthogonal elements (cubes). Unless otherwise noted, piecewise linear interpolation (basis) functions are used to interpret the values of molecular concentrations and electric potentials between element centers.

Within uniformly sampled orthogonal elements, the first term on the right side of equation (2) can be expressed as the sum of the fluxes entering the volume element from its six adjacent neighbors. This flux is composed of electrodiffusion and membrane transport. Here J is defined as the net molecular flux across any surface of the volume element, and is assumed to be constant over that element boundary.

$$-\nabla(\vec{J}_i) = \text{Area}_{boundary} \cdot [Jx|_{x+} - Jx|_{x-} + Jy|_{y+} - Jy|_{y-} + Jz|_{z+} - Jz|_{z-}] \quad 10)$$

The x, y and z components of the molecular flux Jx, Jy, and Jz are evaluated at the 6 element boundaries by assuming them to be constant across each boundary surface. The molecular fluxes depends on the element boundary conditions as follows (see Table 1). The simulation boundary conditions of either fixed concentration, or of fixed molecular flux are easily applied.

TABLE 1

Discrete formulation for molecular flux

| Boundary Condition | Expression for molecular flux |
|---|---|
| Similar Elements | $Jx\|_{x+} = -D_i \nabla C\|_{x+} - z_i \mu_i C_i \nabla V\|_{x+}$ $= D_i \dfrac{C_i(x) - C_i(x+1)}{\Delta x} + z_i \mu_i \cdot C_i\|_{x+} \cdot \dfrac{V(x) - V(x+1)}{\Delta x}$ |
| Dissimilar Elements (membrane) | $Jx\|_{x+}$ = flux due to membrane transport $= f(C_1, C_2, \ldots C_N, V)$ |
| Simulation Boundary (specfiied conc.) | $Jx\|_{x+} = -D\nabla C\|_{x+} = D\dfrac{C(x) - C_{boundary}}{\Delta x / 2}$ |
| Simulation Boundary (specified flux) | $Jx\|_{x+} = J_{boundary}$ |

The numerical approach is described by considering a simplified equation in terms of molecular flux J and source term S.

$$\frac{\partial C}{\partial t} = -\nabla \cdot \vec{J} + S \quad \text{11)}$$

next, this equation is integrated over the time interval and over the volume of an element.

$$\int_t^{t+\Delta t} \int_{x-}^{x+} \int_{y-}^{y+} \int_{z-}^{z+} \frac{\partial C}{\partial t} dz\,dy\,dx\,dt = \Delta x \Delta y \Delta z (C_p - C_p^{old}) \quad \text{12)}$$

$$\int_t^{t+\Delta t} \int_V (-\nabla \cdot \vec{J} + S) dv\,dt = \Delta t \{\Delta y \Delta z (J_{x-} - J_{x+}) + \Delta x \Delta z (J_{y-} - J_{y+}) + \Delta x \Delta y (J_{z-} - J_{z+}) + \Delta x \Delta y \Delta z S\}$$ 13)

so, $$\frac{vol}{\Delta t}(C_p - C_p^{old}) = \quad \text{14)}$$
$$\text{area} \cdot (J_{x-} - J_{x+} + J_{y-} - J_{y+} + J_{z-} - J_{z+}) + vol \cdot \text{Source}$$

for internal elements, a molecular flux defined at x+($J_{x+}$) is defined as follows:

$$J_x|_{x+} = -D_i \nabla C|_{x+} - z_i \mu_i C_i \nabla V|_{x+} \quad \text{15)}$$
$$= D_i \frac{C_i(x) - C_i(x+1)}{\Delta x} + z_i \mu_i \cdot C_i|_{x+} \cdot \frac{V(x) - V(x+1)}{\Delta x}$$

$$\frac{h^3}{\Delta t}(C_p - C_p^{old}) = D \cdot h(C_E - C_P) + \mu \cdot h \cdot \frac{C_E + C_P}{2} \cdot (V_E - V_P) + \quad \text{16)}$$
$$D \cdot h(C_W - C_P) + \mu \cdot h \cdot \frac{C_W + C_P}{2} \cdot (V_W - V_P) +$$
$$D \cdot h(C_N - C_P) + \mu \cdot h \cdot \frac{C_N + C_P}{2} \cdot (V_N - V_P) +$$
$$D \cdot h(C_S - C_P) + \mu \cdot h \cdot \frac{C_S + C_P}{2} \cdot (V_S - V_P) +$$
$$D \cdot h(C_F - C_P) + \mu \cdot h \cdot \frac{C_F + C_P}{2} \cdot (V_F - V_P) +$$
$$D \cdot h(C_B - C_P) + \mu \cdot h \cdot \frac{C_B + C_P}{2} \cdot (V_E - V_P) +$$
$$h^3 \cdot \text{Source}$$

The terms of C are collected to form the matrix coefficients (Equ: 17)

$$A_P C_P + A_E C_E + A_W C_W + A_N C_N + A_S C_S + A_F C_F + A_B C_B = \quad \text{18)}$$
$$B + A_{P0} C_P^{old}$$

where: $A_P = A_{P0} - h^3 \cdot S_{proportional} + \sum_\alpha A_\alpha \quad A_{P0} = \frac{h^3}{\Delta t}$ $$A_\alpha = \begin{cases} D \cdot h & \text{no membrane at } \alpha \\ D_{membrane} \cdot h & \text{membrane at } \alpha \end{cases}$$

$$B = h^3 \cdot S_{constant} + h^2 \cdot \sum_\alpha Jm_\alpha + h \cdot \sum_\alpha B_\alpha$$

$$B_\alpha = \begin{cases} \mu z \frac{C_P + C_\alpha}{2}(V_\alpha - V_P) & \text{no membrane at } \alpha \\ \mu_{membrane} \cdot z \frac{C_P + C_\alpha}{2}(V_\alpha - V_P) & \text{membrane at } \alpha \end{cases}$$

$$\alpha = E, W, N, S, F, B$$

Where chemical reactions are represented as a first order linearization $S_{constant}$, $S_{proportional}$ where Sp is constrained to be negative for stability reasons. Membrane reactions (in the context of species in solution) is represented by reactions with binding sites on the surface of the membrane, and as fluxes through the membrane. The binding site reactions are treated as in the above case (Sc and Sp). The fluxes are currently represented as some combination of a passive membrane term (defining an effective diffusion and mobility constant) and an arbitrary membrane flux term (Jm) to handle any non-linear terms.

Within an element, the left side of (6) becomes the sum of the average charges due to each molecular species (11). Assuming a linear profile of concentration between adjacent elements, the average concentration $\overline{C}_i$ over an element is computed as a linear combination of the sample concentration of the current element and it's nearest neighbors.

$$\oint_v \left[\sum_i z_i F C_i\right] d = \text{Volume} \cdot \sum_i z_i \overline{FC}_i \quad \text{19)}$$

$$\oint_S \vec{D} \cdot d\vec{S} = \quad \text{20)}$$
$$\text{Area} \cdot [D_x|_{x+} - D_x|_{x-} + D_y|_{y+} - D_y|_{y-} + D_z|_{z+} - D_z|_{z-}]$$

Area and Volume refer to the size of a single element.

The x, y and z components of the electric flux density Dx, Dy, and Dz are evaluated at the 6 element boundaries by assuming them to be constant across each boundary surface. The electric potential of neighboring elements are then related by one of the forms of (Table 2). The simulation boundary conditions of either fixed potential, or of fixed electric field (or electric flux density) are easily applied.

TABLE 2

Discrete formulation for electric flux density

| Boundary Condition | Expression for electric flux density, D |
|---|---|
| Similar Elements | $Dx|_{x+} = -\nabla V|_{x+} \varepsilon = \frac{V(x) - V(x+1)}{\Delta x} \varepsilon$ |
| Dissimilar Elements (capacitive membrane) | $Dx|_{x+} = -\nabla V|_{x+} \varepsilon = \frac{V(x) - V(x+1)}{\text{membrane } \Delta x} \varepsilon_{membrane}$ |

TABLE 2-continued

Discrete formulation for electric flux density

| Boundary Condition | Expression for electric flux density, D |
|---|---|
| Simulation Boundary (specified voltage) | $Dx\|_{x+} = -\nabla V\|_{x+} \varepsilon_{x+} = \dfrac{V(x) - V_{boundary}}{\Delta x/2}\varepsilon$ |
| Simulation Boundary (specified field) | $Dx\|_{x+} = \epsilon_{x+}Ex = \epsilon Ex$ |

The numerical approach is described by considering a simplified equation in terms of molecular flux J and source term S.

$$\frac{\partial C}{\partial t} = -\nabla \cdot \vec{J} + S \quad (21)$$

next, this equation is integrated over the time interval and over the volume of an element.

$$\int_t^{t+\Delta t}\int_{x-}^{x+}\int_{y-}^{y+}\int_{z-}^{z+} \frac{\partial C}{\partial t} dz\,dy\,dx\,dt = \Delta x \Delta y \Delta z(C_p - C_p^{old}) \quad (22)$$

$$\int_t^{t+\Delta t}\int_v (-\nabla \cdot \vec{J} + S) dv\,dt = \Delta t\{\Delta y \Delta z(J_{x-} - J_{x+}) + \Delta x \Delta z(J_{y-} - J_{y+}) + \Delta x \Delta y(J_{z-} - J_{z+}) + \Delta x \Delta y \Delta z S\} \quad (23)$$

$$\frac{vol}{\Delta t}(C_p - C_p^{old}) = \text{area} \cdot (J_{x-} - J_{x+} + J_{y-} - J_{y+} + J_{z-} - J_{z+}) + vol \cdot \text{Source} \quad (24)$$

for internal elements, a molecular flux defined at $x+(J_{x+})$ is defined as follows:

$$J_x\|_{x+} = -D_i \nabla C\|_{x+} - z_i \mu_i C_i \nabla V\|_{x+} \quad (25)$$
$$= D_i \frac{C_i(x) - C_i(x+1)}{\Delta x} + z_i \mu_i \cdot C_i\|_{x+} \cdot \frac{V(x) - V(x+1)}{\Delta x}$$

$$\frac{h^3}{\Delta t}(C_P - C_P^{old}) = D \cdot h(C_E - C_P) + \mu \cdot h \cdot \frac{C_E + C_P}{2} \cdot (V_E - V_P) + \quad (26)$$
$$D \cdot h(C_W - C_P) + \mu \cdot h \cdot \frac{C_W + C_P}{2} \cdot (V_W - V_P) +$$
$$D \cdot h(C_N - C_P) + \mu \cdot h \cdot \frac{C_N + C_P}{2} \cdot (V_N - V_P) +$$
$$D \cdot h(C_S - C_P) + \mu \cdot h \cdot \frac{C_S + C_P}{2} \cdot (V_S - V_P) +$$
$$D \cdot h(C_F - C_P) + \mu \cdot h \cdot \frac{C_F + C_P}{2} \cdot (V_F - V_P) +$$
$$D \cdot h(C_B - C_P) + \mu \cdot h \cdot \frac{C_B + C_P}{2} \cdot (V_E - V_P) +$$
$$h^3 \cdot \text{Source}$$

The terms of C are collected to form the matrix coefficients (Equ: 27)

$$A_P C_P + A_E C_E + A_W C_W + A_N C_N + A_S C_S + A_F C_F + A_B C_B = B + A_{P0} C_P^{old} \quad (28)$$

where: $A_P = A_{P0} - h^3 \cdot S_{proportional} + \sum_\alpha A_\alpha \quad A_{P0} = \dfrac{h^3}{\Delta t}$ -continued $$A_\alpha = \begin{cases} D \cdot h & \text{no membrane at } \alpha \\ D_{membrane} \cdot h & \text{membrane at } \alpha \end{cases}$$

$$B = h^3 \cdot S_{constant} + h^2 \cdot \sum_\alpha Jm_\alpha + h \cdot \sum_\alpha B_\alpha$$

$$B_\alpha = \begin{cases} \mu z \dfrac{C_P + C_\alpha}{2}(V_\alpha - V_P) & \text{no membrane at } \alpha \\ \mu_{membrane} \cdot z \dfrac{C_P + C_\alpha}{2}(V_\alpha - V_P) & \text{membrane at } \alpha \end{cases}$$

$$\alpha = E, W, N, S, F, B$$

Where chemical reactions are represented as a first order linearization $S_{constant}$, $S_{proportional}$ where Sp is constrained to be negative for stability reasons. Membrane reactions (in the context of species in solution) is represented by reactions with binding sites on the surface of the membrane, and as fluxes through the membrane. The binding site reactions are treated as in the above case (Sc and Sp). The fluxes are currently represented as some combination of a passive membrane term (defining an effective diffuision and mobility constant) and an arbitrary membrane flux term (Jm) to handle any non-linear terms.

The modeled chemical reactions include bulk reactions and membrane reactions. All bulk reactions are treated as coupled differential equations describing their reaction rates. Reactions are created such that their behavior is adjusted to interact only with their defined environment. The general form assumed is as follows:

$$aA + bB \underset{k_{-1}}{\overset{k_1}{\rightleftharpoons}} cC + dD \quad (29)$$

$$-\frac{1}{a}\frac{d[A]}{dt} = -\frac{1}{b}\frac{d[B]}{dt} = \frac{1}{c}\frac{d[C]}{dt} = \frac{1}{d}\frac{d[D]}{dt} \quad (30)$$
$$= k_1[A]^n[B]^m - k_{-1}[C]^r[D]^s$$

These relationships are true provided that there are no intermediate species, or if there are intermediates, their concentrations are independent of time for most of the reaction period. In general, the reaction rate for either elementary or multi-step reactions is a nonlinear relation that may be linearized about a set of current conditions.

$$\frac{d[A]}{dt} = -f_{A\_linear}([A], [B], \ldots ) \cdot [A] + f_{A\_constant}([C], [D], \ldots ) \quad (31)$$

A particular simulation may not have defined one or more of the reagents as state variables. The reaction model must then either be disabled or simplified depending on which reagents are missing. A simplified model uses a constant concentration for each missing reagent as defined for that biological feature type. This constant concentration can be specified in the model description or the default value for that feature type will be used.

Figure 6:
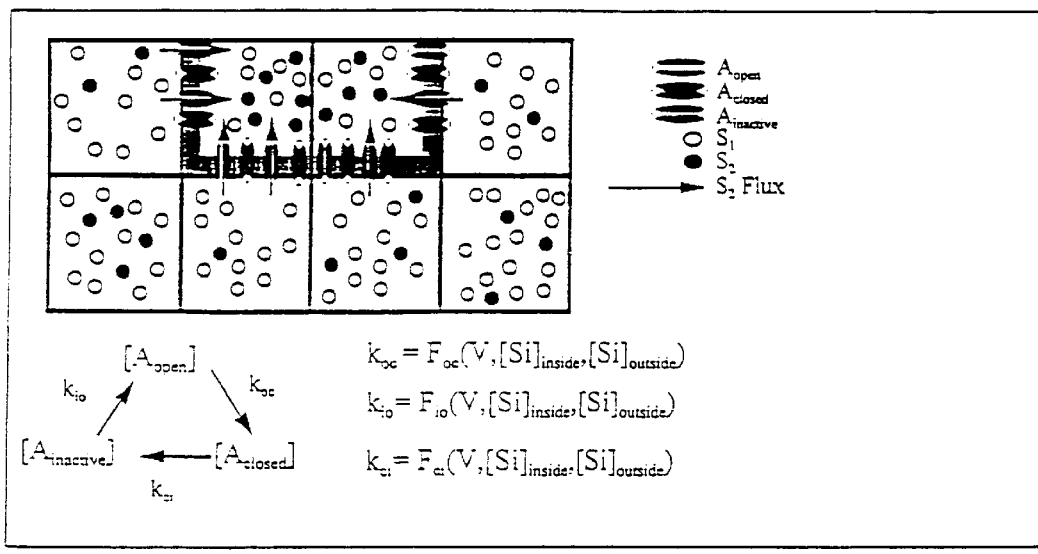
FIG. 6 is a diagram of typical membrane reactions and heir corresponding molecular states.

All-membrane reactions are treated as coupled differential equations describing their reaction rates. These reactions, like bulk reactions, adjust their complexity according to the defined environment of the simulation. Typical membrane reactions are pumps and channels. Each membrane reaction requires a set of one or more corresponding molecules each representing a distinct configuration (state) of the corresponding pump, channel, or carrier (e.g. open, closed, inactive). FIG. 6 illustrates the modeling of the various membrane reaction states. A membrane reaction state represents a significant combination of bindings and conformations of a pump or channel needed to describe its dynamic behavior. This allows a model of channel or pump dynamics to incorporate discrete states such as open, closed, and inactive. The state transitions are defined in terms of reaction rate equations that can be functions of membrane potential and species concentrations on either side of the membrane. The equations are written such that the stoichiometry of the whole model is consistent and that flux is conserved.

These states are defined in terms membrane surface densities and can be represented by state variables or by constants. There is only one value of the surface density of a membrane variable that is defined for each element, although an element may have up to 6 separate membrane surfaces. Reaction rates on membrane variables (channels and pumps) are averaged over the membrane surfaces of an element. Missing reagents are handled in a manner similar to that of the bulk reactions defined above. An important additional requirement of the trans-membrane reactions is that flux be conserved.

Species on either side of a membrane can be effected by membrane reactions in two ways. The first is to pass through the channel or pump as membrane flux. The second is to react with a binding site on a membrane molecule, causing a membrane reaction state transition. These reactions are governed by the membrane reaction states, the potential difference across the membrane, and the concentrations of one or more species on either side of the membrane. Channels can in principle have receptor sites on either or both sides of the membrane. The conservation of flux can be used as one of the convergence criteria for the numerical solution.

The treatment of membrane channel and pump surface densities assumes a single value for each element, representing the average over all that element's membrane boundaries. This defines a single (average) concentration over all membrane surface patches connected to a single element. An alternative is to define two dimensional membrane patches. Thus, an element boundary that is associated with a membrane will reference that two dimensional membrane patch.

Figure 7:
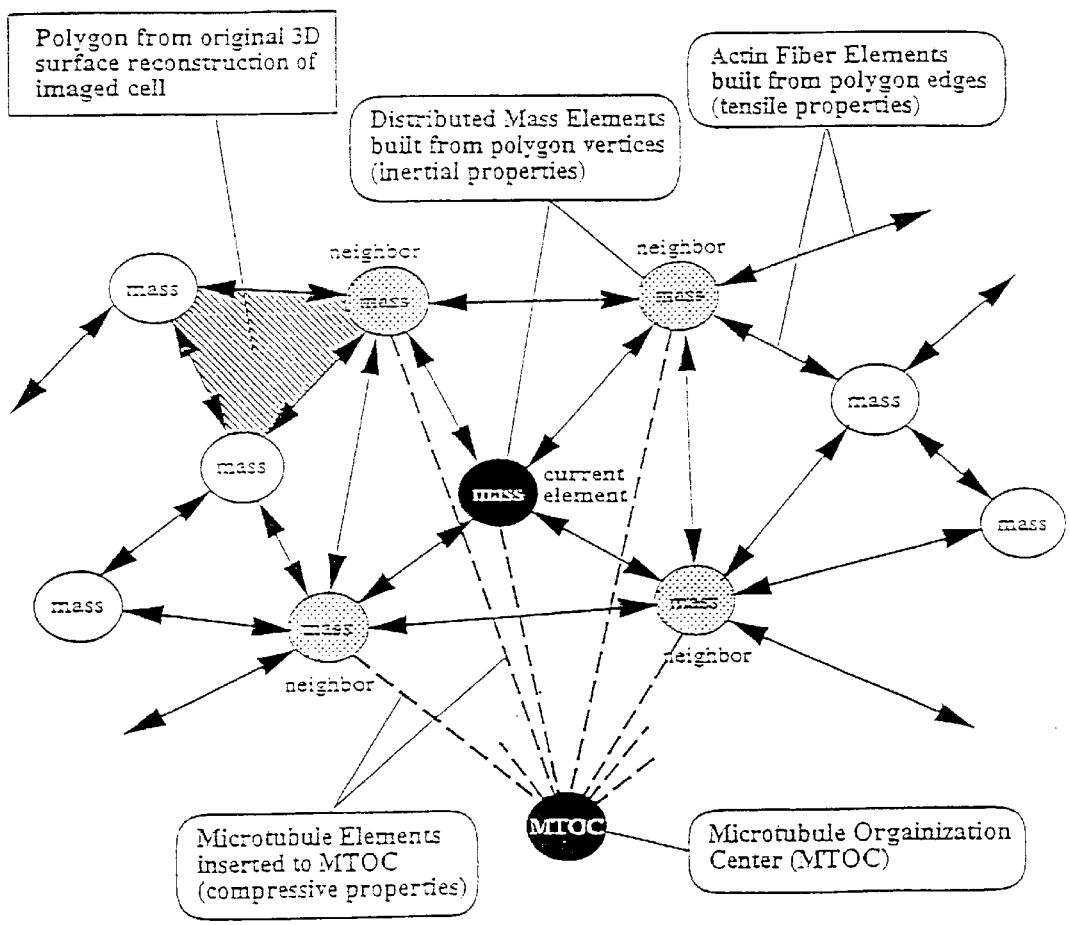
FIG. 7 is an illustration of mechanical simulation elements.

The modeling of mechanical dynamics requires a mesh of connected elements where each element interacts with its neighbors through applied forces and each element reacts according to applicable equations of motion. An exemplary simulation mesh is based on use of an iso-surface reconstruction. The corresponding mechanical model describes cell membrane movement as tensile, compressive and viscous forces acting on distributed inertial masses. FIG. 7 illustrates a polygonal mesh from a surface reconstruction of three dimensional data set of a cell which is used as the basis for a mechanical simulation of membrane characteristics. The geometry of the polygonal mesh is based on actual volume data. It is understood that the geometry of the surface model can be based on an iso-surface reconstruction of a three dimensional microscopy image, or any other polygonal surface model. Thus, the simulated polygonal surface can be rendered in three dimensions and compared with results from experimental micro-manipulation of the same cell. The mechanical dynamics can be with alternative techniques such as finite element analysis.

A large collection of reaction models will be necessary to support simulations of various cell lines and physiological problems. Membrane reaction models and local reaction models are maintained as reaction descriptions, which define the reaction rates of certain molecular species as a function of the local environment. Each description consists of a set of rate expressions that are functions of model variables and parameters (e.g. reaction rates, pump rates, etc.). These descriptions are stored in a database, and when needed, $C^{++}$ code is automatically generated to create a simulation specific model object library. This allows users to specify new models without any programming experience, and with little regard for the underlying numerical methods. In addition, upgrades of simulation software architecture will not affect the configuration management of reaction model descriptions.

A database of specific and customizable reactions and membrane mechanisms may be made available for building cellular models through a central repository. A naming standard for both models and molecular species must be created to allow models to be inter- operable. The selected models are then automatically combined to form a single reaction rate for each molecular species in each feature. These rates are automatically coded, compiled and linked with the simulation framework. A user could access the repository to retrieve the customizable simulations of reactions and membrane mechanisms. The user the combines these components to form the cellular model.

When building an integrated cellular model from an arbitrary collection of individual reaction models, care must be taken to achieve a consistent initial condition. Many simulations take the form of homeostasis (steady state) perturbed by some stimulus (system input). It is generally beneficial to separate the forced response of the simulation (response due to the input) from the natural response of the simulation (response due to the initial conditions with no input). To look at the forced response (of most interest), the initial conditions should be balanced such that all of the variables are set to appropriate steady state values. This is generally not a trivial task for a newly generated collection of individual models with user defined initial values of molecular species and potential.

The approach taken to address this issue is a constrained optimization of model and feature parameters. Model parameters include individual reaction rates, binding rates, pump flux constants or any "constant" used to describe the dynamics of the modeled mechanism. Feature parameters include initial concentrations of molecular species, surface densities of membrane species, and electric potential defined for that feature. Any parameter is described in terms of a probability distribution over its allowable values. For a particular application, if a parameter is perturbed from its most probable (nominal) value, then a penalty function is evaluated. This penalty is generally inversely proportional to it's normalized probability distribution. An overall penalty function is generated as a weighted sum of individual penalty functions, where the weights are determined by the users, and reflect the confidence in the accuracy of each parameter's distribution.

A non-linear optimization is performed to minimize the steady state net reaction rates and fluxes while also minimizing the total penalty function. This optimization process is interactive, allowing the user to update confidence and distribution functions such that the simulation best matches the desired physiological situation. This allows homeostasis to be achieved in an orderly fashion with the tradeoffs being driven from the user's experience and knowledge. In an exemplary embodiment, the invention uses a conjugate gradient search algorithm to find the local minimum based on initial parameter values. A more robust algorithm may incorporate a Monte Carlo method of generating the initial parameter space vectors such that the best local minimum may be comparable to the global minimum.

The simulation framework can periodically store the values of the state variables to files called simulation dumps. Each simulation dump uniquely represents the simulated physiology at a discrete point in time. Any state variable can easily visualized over space and time using tools that are compatible with the simulation dump files.

In addition to state variables, the models can be used in the post-processing of the data to determine some derived states. Derived states are reaction rates, fluxes, or anything else that can be expressed in terms of the state variables. Which means, by the definition of state variables, that anything that is represented in the models can be reconstructed after the simulation via the simulation dumps. This enables a very flexible post-processing capability. This capability is enabled by the software architecture, which is object oriented and very modular such that these questions can be asked within the framework without making the individual models complex.

Geometric models and simulation elements can both be displayed within an integrated 3D viewer. The model can be displayed as a set of polygonal surfaces that can be quickly manipulated with accelerated graphics. The state variable values within the simulation elements are then volume rendered into the same scene as the surface model. A more general multivariate, four dimensional data analysis package is needed to properly analyze the data.

The simulation results are currently associated with the model description and a simulation log file. A database of either containing or citing simulation models, results, and conclusions would be very helpful in the process of cooperative research. In this way, individual and aggregate models and their associated parameters can be evaluated, and confidence in parameter usage can be determined. This type of situation will work well if users make their results freely available to others.

Figure 8:
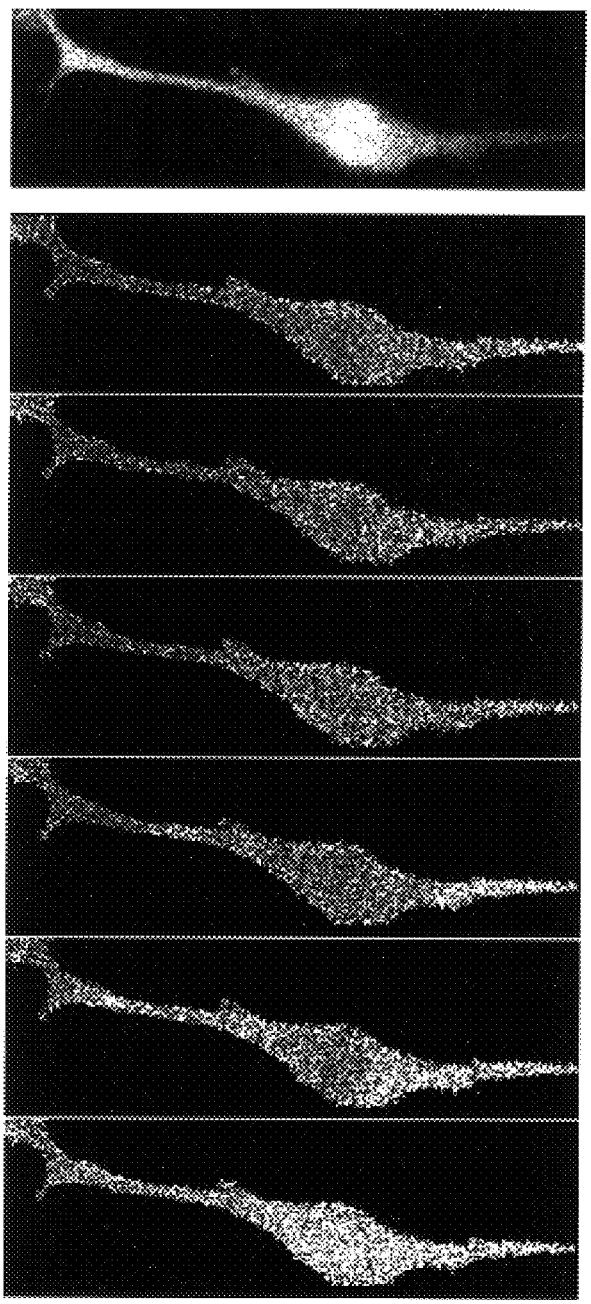
FIG. 8 is a series of images of an actual cell.
Figure 9:
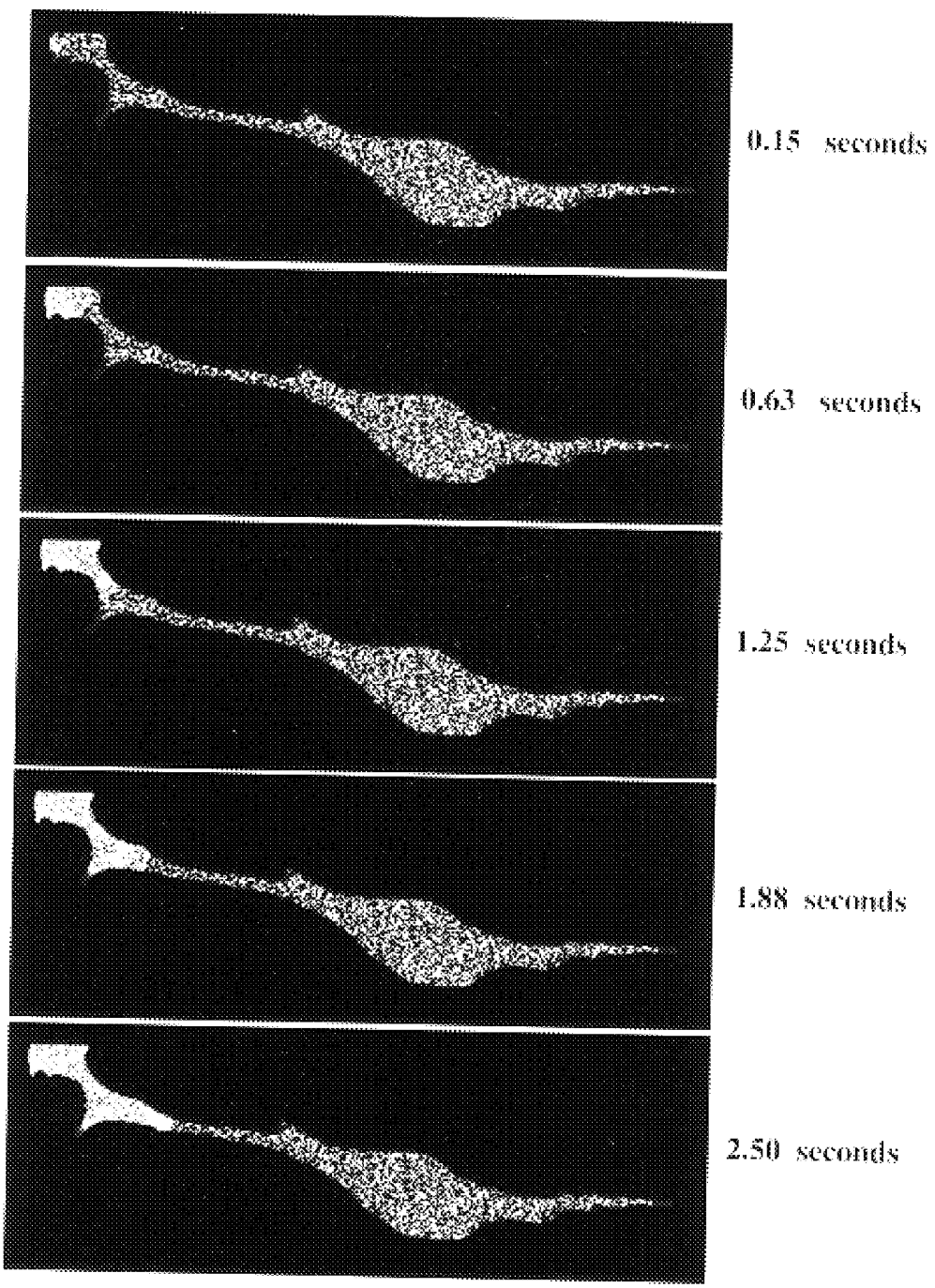
FIG. 9 is a series of images of a simulated cell corresponding to the actual data in FIG. 8.

Example simulations have been generated involving the calcium induced calcium dynamics involving the IP3 receptor in neuroblastoma cells. FIG. 8 is a time series of experimental images of mouse neuroblastoma loaded with a calcium indicator. The images shown in FIG. 8 are two dimensional slices of a fluorescence microscopy image of the cell. The concentration of calcium was image at regular intervals during an experiment designed to observe calcium dynamics. FIG. 9 is a series of simulation images corresponding to the actual images shown in FIG. 8. FIG. 9 shows a series of two dimensional slices of a chemical simulation volume. The simulation modeled a wave of increased free calcium ion concentration due to intracellular triggering event. Because the simulation geometry was generated based on the actual cell image, the simulation data of FIG. 9 is easily compared to the experimental data shown in FIG. 8. The model geometry was taken directly from a microscope image of the cell in question, and the model was built with a collection of individual models of physiology from the literature.

Figure 10:
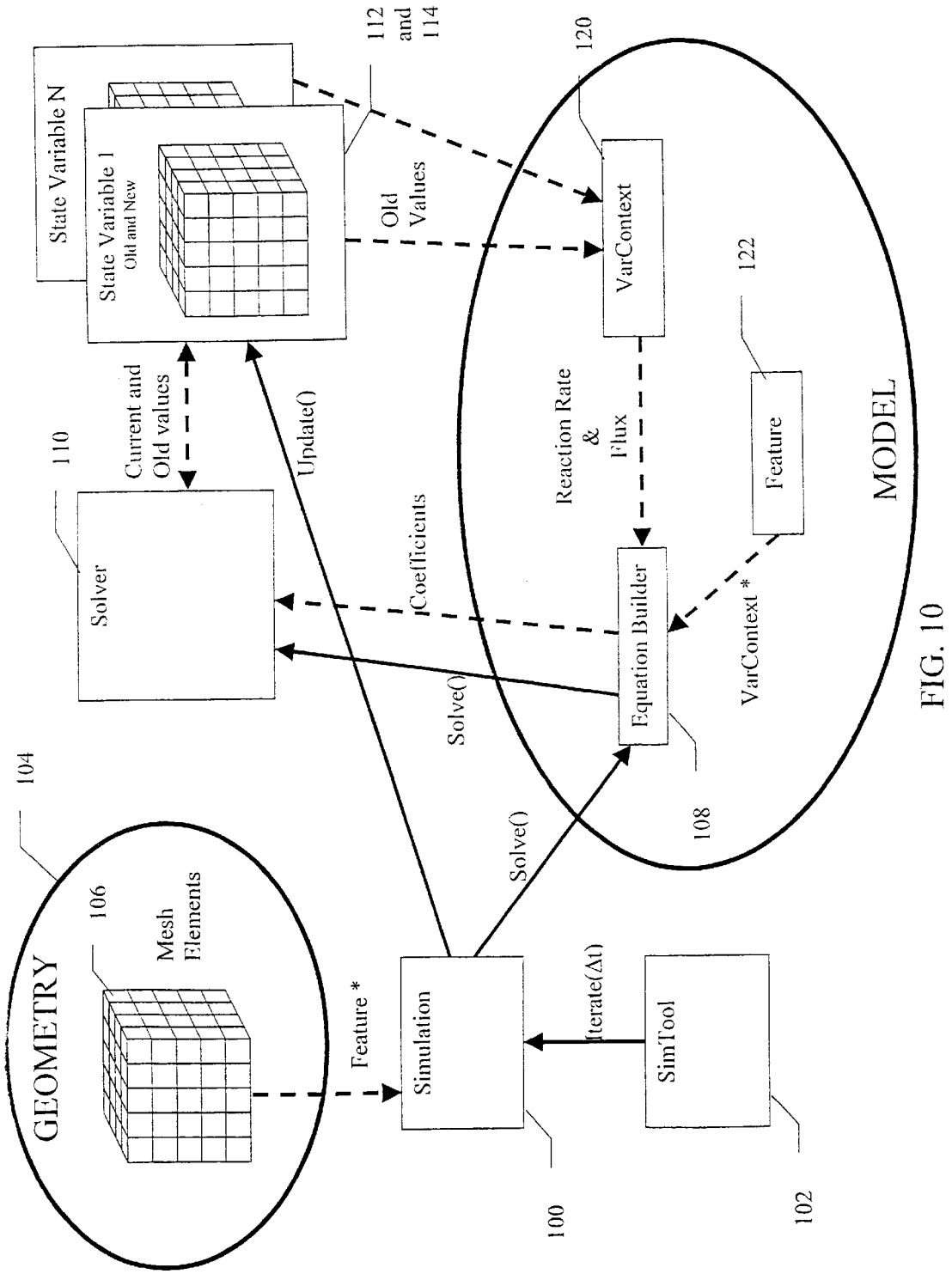
FIG. 10 is a control flow diagram for the simulation.

FIG. 10 is a flow control diagram illustrating a number of modules that combine to form a simulator that implements the simulation. The simulation may be implemented on a general purpose computer or in dedicated hardware having software (firmware) associated therewith or a combination of software and hardware. As shown in FIG. 10, a simulation module 100 controls the progress of the simulation. The simulation module 100 controls the timing of the simulation and transfers data to and from other portions of the simulator and provides overall control for the execution of the simulation. The simtool module 102 receives user commands and provides the commands to the simulation module 100. A simulation mesh 104 is a three dimensional array of simulation elements 106. The simulation elements 106 are each associated with a feature object 122 which identifies the physiological features of the simulation element 106. Current state variables 112 and past state variables 114 are stored and are provided to a solver 110, along with information from the equation builder 108 to update the state variables of the simulation. The solver 110, the equation builder 108 and the state variable storage 112 and 114 are all connected to the simulation module 100 for control purposes. The varcontext module 120 maintains the reaction rates for a specific species and is referenced by the cellular feature 122. For example, if the simulation element 106 corresponds to cytoplasm then the simulation element 106 is linked to a feature 122 corresponding to the cytoplasm. The varcontext module 120 stores the net reaction rate for a particular variable for the cytoplasm. In this way, the user knows which reactions may be simulated for a particular cell feature and time is not wasted searching for available reactions.

The simulator shown in FIG. 10 first initializes the simulation by performing the following operations.
determine initial iteration time
load default values into variables
initialize variable contexts
if applicable, calculate charge and initialize potential Upon each iteration of the simulation, the simulation framework performs the following operations. do the following until maximum normalized error <1 or max iterations reached.
  (a) for each variable, do the following
    (1) for each element, do the following
      (i) get feature
      (ii) get corresponding varcontext data
      (iii) ask for reaction rates and fluxes for current variable at current element
      (iv) form coefficients based on equation builder
    (2) solve implicit matrix equation for PDE's or explicit ODE equation
  (b) if potential defined, solve for potential using equations 8 and 9
  (c) update variable values The present invention provides a framework that is a very general and flexible simulation tool that allows researchers to build on the experimental results and theoretical evaluations of others in an effort to better understand the interactions of cellular physiology. As related models are verified under various conditions and different cell lines, generalizations of related phenomena can be quantified in a structured way. In this way, individual researchers can use this as a tool to better understand their physiological application, while at the same time contributing to a shared knowledge base for the benefit of all. Although the invention has been described as a simulation method for cells, it is understood that the invention may be applied to the simulation of multiple cells (e.g. tissue). In addition, the simulation method is not limited to the simulation of biological events but may be applied to variety of real world events such as modeling electromechanical gas sensors with different geometry or interfaces to air. The chemical dynamics of any chemical process can be simulated using the method of the present invention. Accordingly, the invention has application beyond cellular simulations.

While preferred embodiments have been shown and described, various modifications and substitutions may be made thereto without departing from the spirit and scope of the invention. Accordingly, it is to be understood that the present invention has been described by way of illustration and not limitation.

What is claimed is:

1. A method of simulating a biological material comprising:

acquiring an n-dimensional geometric description of the biological material;

linking at least one biological feature to a feature model defining physiological properties of said feature, said feature model defning a spatially independent feature model;

associating said feature model with a region within said n-dimensional geometric description, thereby specifying a set of mathematical equations corresponding to processes in said region;

creating a set of simulation elements defining a simulation volume from said n-dimensional description, each of said simulation elements corresponding to one of said regions; and simulating a physiological process for said biological material through said simulation elements, said simulation elements providing for the spatial discretization of said mathematical equations.

2. The method of simulating a biological material of claim 1 wherein said n-dimensional description is an image and said region is identified by thresholding the image and segmenting the image.

3. The method of simulating a biological material of claim 1 wherein said model indicates chemical dynamics for said simulation element.

4. The method of simulating a biological material of claim 1 wherein said model indicates mechanical dynamics for said simulation element.

5. The method of simulating a biological material of claim 1 further comprising producing a simulated n-dimensional description of the result of said simulating a physiological property for said simulation elements.

6. The method of simulating a biological material of claim 5 wherein said n-dimensional description and said simulated n-dimensional description are mapped to a single coordinate system.

7. The method of simulating a biological material of claim 1 wherein said n-dimensional description is a three dimensional image.

8. The method of simulating a biological material of claim 5 wherein said simulated n-dimensional description is a three dimensional image.

9. The method of simulating a biological material of claim 1 wherein said simulation elements have the same size.

10. The method of simulating a biological material of claim 1 wherein said simulation elements have the same shape.

11. The method of simulating a biological material of claim 1 wherein said biological material includes cellular structure, said cellular structure having a predetermined size is represented by predefined geometry.

12. The method of simulating a biological material of claim 11 wherein said predefined geometry is a geometric primitive.

13. The method of simulating a biological material of claim 11 wherein said predefined geometry is a mathematically defined solid.

14. The method of simulating a biological material of claim 11 wherein said predefined geometry is a polygonal surface.

15. The method of simulating a biological material of claim 1 wherein said biological material includes cellular structure; said cellular structure being modeled to be distributed through said biological material.

16. The method of simulating a biological material of claim 1 wherein said simulation element is a region in the biological material.

17. The method of simulating a biological material of claim 16 wherein said model defines physiological properties of said region for a plurality of geometries.

18. The method of simulating a biological material of claim 1 wherein cellular structure having a predetermined shape is represented by predefined geometry.

19. The method of simulating a biological material of claim 18 wherein said predefined geometry is a geometric primitive.

20. The method of simulating a biological material of claim 18 wherein said predefined geometry is a mathematically defined solid.

21. The method of simulating a biological material of claim 18 wherein said predefined geometry is a polygonal surface.

22. The method of claim 1 wherein said geometric description includes a plurality of regions and said feature model is associated with a plurality of regions.

* * * * *